United States Patent [19]

Duffett

[11] Patent Number: Plant 6,232

[45] Date of Patent: Jul. 26, 1988

[54] CHRYSANTHEMUM PLANT NAMED OVARO

[75] Inventor: William E. Duffett, Salinas, Calif.

[73] Assignee: Yoder Brothers, Inc., Barberton, Ohio

[21] Appl. No.: 833,177

[22] Filed: Feb. 26, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Ovaro particularly characterized by its flat capitulum form; anemone capitulum type; yellow ray floret color with a bronze overcast when grown under low light and low temperature conditions; diameter across face of capitulum of up to 12 cm. at maturity when grown as a pinched disbudded pot mum, with diameter of anemone cushion of up to 4 cm.; uniform eight week photoperiodic flowering response to short days; tall plant height when grown as a pinched pot mum; recommended both as disbudded and spray pot mum; and spreading branching pattern.

3 Drawing Sheets

The present invention comprises a new and distinct cultivar of Chrysanthemum, botanically known as *Dentrenthema morifolium*, Ramat., previously *Chrysanthemum morifolium*, Ramat., and referred to by the cultivar name Ovaro.

Ovaro, identified as 79U03004, was originated from a cross made by me in a controlled breeding program in Salinas, Calif., in 1979. The female parent of Ovaro was the cultivar identified as Pert, disclosed in U.S. Plant Pat. No. 4,764. The male parent of Ovaro, identified as 78-19015, was an unnamed seedling.

Ovaro was discovered and selected as one flowering plant within the progeny of the stated cross by William E. Duffett in November of 1980, in a controlled environment in Salinas, Calif.

The first act of asexual reproduction of Ovaro was accomplished when vegetative cuttings were taken from the initial selection in February of 1981 in a controlled environment in Salinas, Calif. by technicians working under formulations established and supervised by William E. Duffett.

Horticultural examination of controlled flowerings of successive plantings has shown that the unique combination of characteristics as herein disclosed for Ovaro are firmly fixed and are retained through successive generations of asexual reproduction.

Ovaro has not been observed under all possible environmental conditions. The phenotype may vary significantly with variations in environment such as temperature, light intensity and day length.

The following observations, measurements and comparisons describe plants grown in Salinas, Calif. and Leamington, Canada under greenhouse conditions which approximate those generally used in commercial greenhouse practice.

The following traits have been repeatedly observed and are determined to be basic characteristics of Ovaro which, in combination, distinguish this Chrysanthemum as a new and distinct cultivar:

1. Flat capitulum form.
2. Anemone capitulum type.
3. Yellow ray floret color with a bronze overcast when grown under low light and low temperature conditions.
4. Diameter across face of capitulum up to 12 cm. at maturity when grown as a pinched disbudded pot mum, with the diameter of the the anemone cushion being up to 4 cm.
5. Uniform eight week photoperiodic flowering response to short days.
6. Tall plant height, requiring no long days after pinch prior to short days and one application of 2500 ppm B-9 SP to attain a flowered plant height of 25 to 35 cm. for year around flowerings when grown as a pinched pot mum.
7. Recommended both as disbudded and spray pot mum.
8. Spreading branching pattern.

The accompanying photographic drawings show typical inflorescence and leaf characteristics of Ovaro, with the colors being as nearly true as possible with illustrations of this type.

Sheet 1 is a color photograph of Ovaro grown as a pinched disbudded pot mum.

Sheet 2 is a black and white photograph of three views of the inflorescence of Ovaro.

Sheet 3 is a black and white photograph showing the upper and under sides of the leaves of Ovaro at three stages of development (mature, intermediate and immature).

Of the commercial cultivars known to the inventor, the most similar in comparison to Ovaro is Cymbals, disclosed in U.S. Plant Pat. No. 5,019. Reference is made to attached Chart A, which compares certain characteristics of Ovaro to the same characteristics of Cymbals. Similar traits are capitulum form and branching pattern. Ovaro has an anemone capitulum type versus the single capitulum type of Cymbals. Ovaro has a smaller flower, a taller plant height and a shorter flowering response to short days than Cymbals. Ovaro is recommended as a disbudded and spray pot mum, while Cymbals is only recommended as a disbud pot mum.

In the following description, color references are made to The Royal Horticultural Society Colour Chart. The color values were determined on plant material grown in Salinas, Calif. on July 19, 1985. The color values of the ray floret color were determined on plants grown under high light conditions under which the bronze overcast, which develops under low light and low temperatures, was not evident.

Classification:

*Botanical.*—*Dentrenthema morifolium,* Ramat., cv Ovaro.

*Commercial.*—Anemone disbud and spray pot mum.

INFLORESCENCE

A. Capitulum:

*Form.*—Flat.

*Type.*—Anemone.

*Diameter across face.*—Up to 12 cm. at maturity with diameter of anemone cushion of up to 4 cm.

B. Corolla of ray florets:

*Color (general tonality from a distance of three meters).*—Yellow.

*Color (upper surface).*—11B to 12B, with a slight bronze overcast.

*Color (under surface).*—9B.

*Shape.*—Oblong.

C. Corolla of disc florets.

*Color (mature).*—14A.

*Color (immature).*—2B.

D. Reproductive organs:

*Androecium.*—Present disc florets only; scant pollen.

*Gynoecium.*—Present both ray and disc florets.

PLANT

A. General appearance:

*Height.*—Tall; 25 to 35 cm. as a pinched pot mum with no long days after pinch prior to short days and one application of 2500 ppm B-9 SP.

*Branching pattern.*—Spreading and prolific.

B. Foliage:

*Color (upper surface).*137A.

*Color (under surface).*—138B.

*Shape.*—Lobed and slightly serrated.

CHART A

COMPARISON OF OVARO AND CYMBALS

| CULTIVAR | RAY FLORET COLOR | CAPITULUM FORM & TYPE | BRANCHING PATTERN | DIAMETER ACROSS FACE OF CAPITULUM |
|---|---|---|---|---|
| Ovaro | Yellow With Bronze Overcast | Flat Anemone | Spreading | Up to 12 Cm. |
| Cymbals | Golden Bronze | Flat Single | Spreading | 125 to 140 mm. |

| CULTIVAR | PLANT HEIGHT | FLOWERING RESPONSE PERIOD | RECOMMENDED USE |
|---|---|---|---|
| Ovaro | Tall | 8 Weeks | Disbud & Spray |
| Cymbals | Medium | 9 Weeks | Disbud Only |

COMPARISONS MADE OF PLANTS GROWN AS PINCHED DISBUDDED POT MUMS IN SALINAS, CALIFORNIA

I claim:

1. A new and distinct Chrysanthemum plant named Ovaro, as described and illustrated, and particularly characterized as to uniqueness by the combined characteristics of flat capitulum form; anemone capitulum type; yellow ray floret color with a bronze overcast when grown under low light and low temperature conditions; diameter across face of capitulum of up to 12 cm. at maturity when grown as a pinched disbudded pot mum, with diameter of anemone cushion of up to 4 cm.; uniform eight week photoperiodic flowering response to short days; tall plant height when grown as a pinched pot mum; recommended both as disbudded and spray pot mum; and spreading branching pattern.

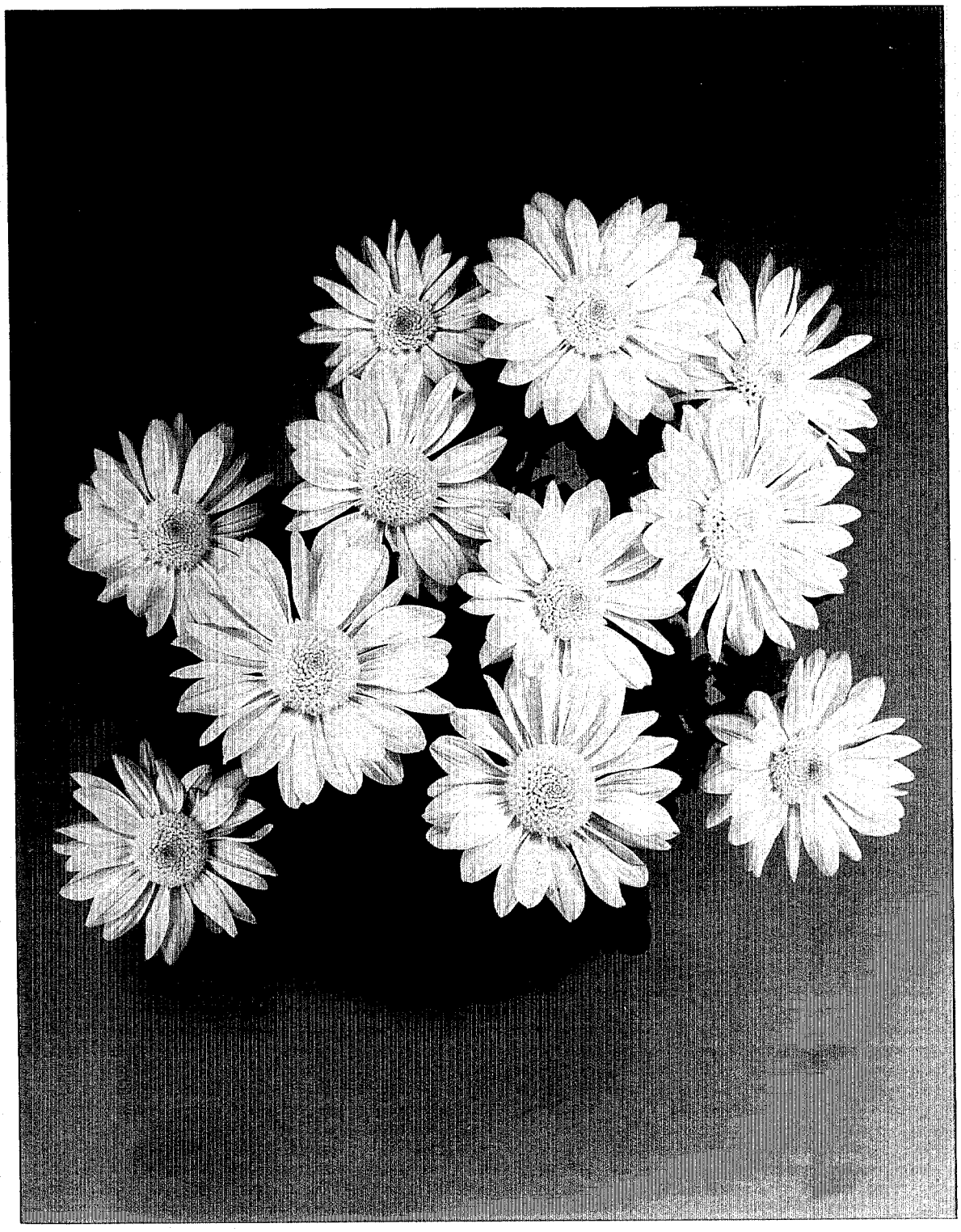

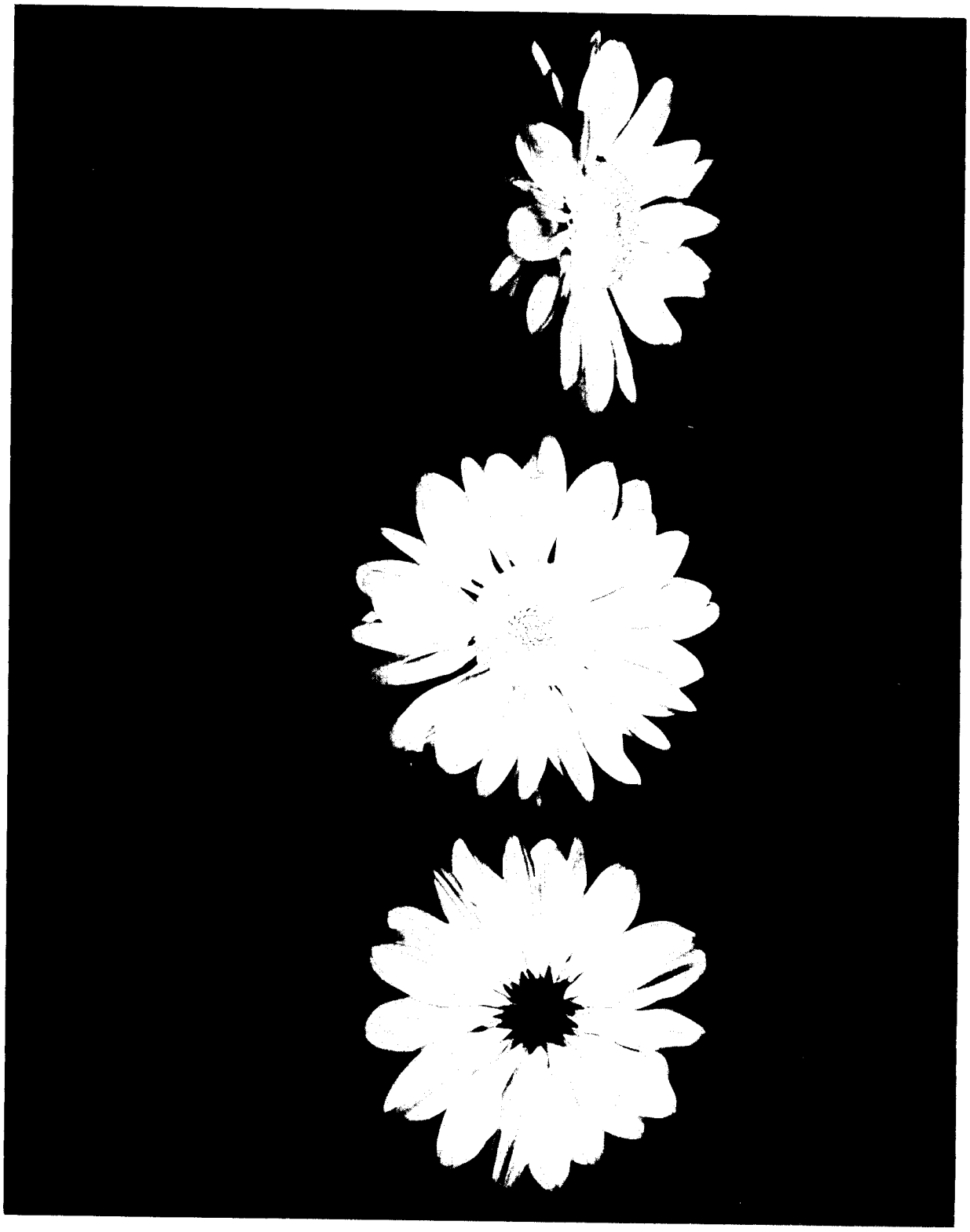

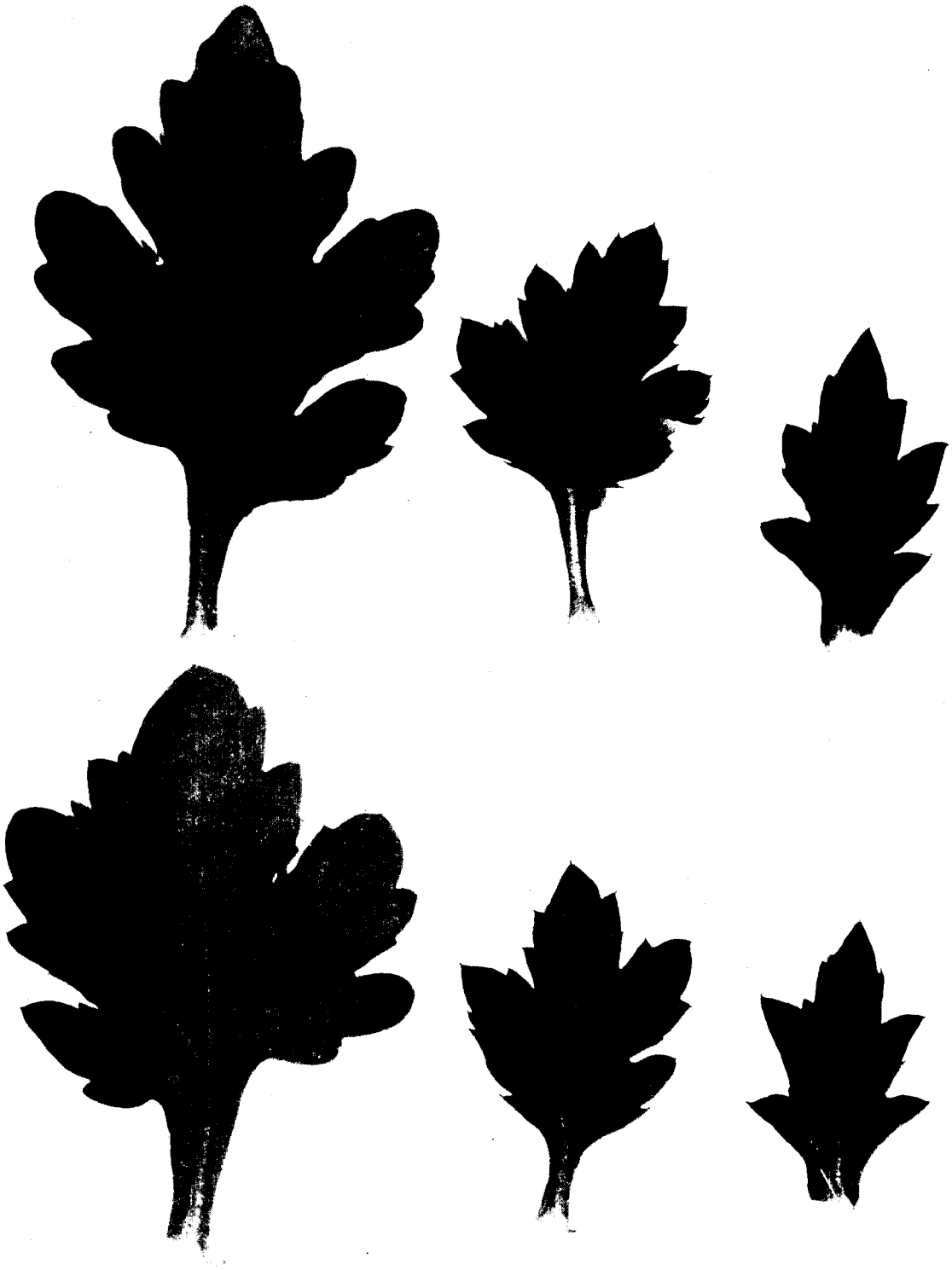

* * * * *